United States Patent
Ravi Kumar et al.

(10) Patent No.: US 11,214,551 B2
(45) Date of Patent: Jan. 4, 2022

(54) ONE POT SYNTHESIS OF 4-(1,2-DIHYDRO-2-OXOBENZO[D]IMIDAZOL-3-YL)BUTANOIC ACID, A KEY INTERMEDIATE OF ZILPATEROL

(71) Applicant: RA CHEM PHARMA LIMITED, Hyderabad (IN)

(72) Inventors: Kannasani Ravi Kumar, Hyderabad (IN); Kasa Mallik Yadav, Hyderabad (IN); Mulu Sreenu, Hyderabad (IN); V. V. V Babu, Pulletikurru (IN)

(73) Assignee: RA CHEM PHARMA LIMITED, Hyderabad (IN)

( * ) Notice: Subject to any disclaimer, the term of this patent is extended or adjusted under 35 U.S.C. 154(b) by 0 days.

(21) Appl. No.: 17/050,867

(22) PCT Filed: Mar. 4, 2019

(86) PCT No.: PCT/IN2019/050186
§ 371 (c)(1),
(2) Date: Oct. 27, 2020

(87) PCT Pub. No.: WO2019/207591
PCT Pub. Date: Oct. 31, 2019

(65) Prior Publication Data
US 2021/0238146 A1    Aug. 5, 2021

(30) Foreign Application Priority Data
Apr. 27, 2018   (IN) .............................. 201841016014

(51) Int. Cl.
*C07D 235/26*   (2006.01)

(52) U.S. Cl.
CPC .................................. *C07D 235/26* (2013.01)

(58) Field of Classification Search
CPC ..................................................... C07D 235/26
See application file for complete search history.

(56) References Cited

FOREIGN PATENT DOCUMENTS

| | | |
|---|---|---|
| CN | 102603650 A | 7/2012 |
| EP | 2535340 A2 | 12/2012 |

*Primary Examiner* — Shawquia Jackson
(74) *Attorney, Agent, or Firm* — Simpson & Simpson, PLLC; Michael Nicholas Vranjes

(57) ABSTRACT

The present invention relates to one pot process for the preparation of 4-(1,2-dihydro-2-oxobenzo[d]imidazol-3-yl) butanoic acid of Formula-I, which is a key intermediate and its use in the preparation of Zilpaterol, which comprises condensation of methyl-4-chloro butyrate with 1-(prop-1-en-2-yl)-1H-benzo[d]imidazol-2(3H)-one in presence of a base and suitable solvent to give corresponding ester derivative, further hydrolyzation and acidification in presence of inorganic solvent to obtain Formula-I.

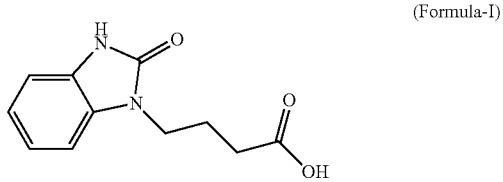

(Formula-I)

7 Claims, No Drawings

ONE POT SYNTHESIS OF 4-(1,2-DIHYDRO-2-OXOBENZO[D]IMIDAZOL-3-YL)BUTANOIC ACID, A KEY INTERMEDIATE OF ZILPATEROL

TECHNICAL FIELD

The present invention relates to an improved process for the preparation of 4-(1,2-dihydro-2-oxobenzo[d]imidazol-3-yl)butanoic acid from 1-(prop-1-en-2-yl)-1H-benzo[d]imidazol-2(3H)-one which is used as a key intermediate for the preparation of Zilpaterol.

More particularly, the invention relates to an eco-friendly and cost-effective process with shorter reaction time, which provides 4-(1,2-dihydro-2-oxobenzo[d]imidazol-3-yl)butanoic acid with high yield and purity.

BACKGROUND ART

The 4-(1,2-dihydro-2-oxobenzo[d]imidazol-3-yl)butanoic acid of formula (I) is a benzimidazole derivative,

[chem. 1]

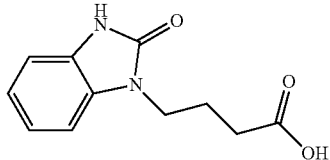

(Formula-I)

and is one of the key intermediate in zilpaterol manufacturing process.

Zilpaterol code named as RU 42173 is a β₂ adrenergic agonist under its trade name Zilmax, it is used to increase the size of cattle and the efficiency of feeding them. Zilmax is produced by Intervet, a subsidiary of Merck & Co., and marketed as a "beef-improvement technology". Zilapterol is chemically represented as 4,5,6,7-tetrahydro-7-hydroxy-6-(isopropylamino)imidazo[4,5,1-jk][1]benzazepin-2(1H)-one having a structural formula as follows:

[Chem. 2]

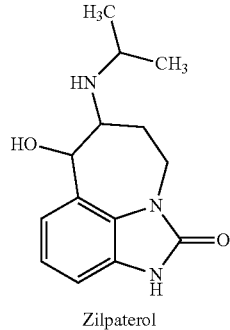

Zilpaterol

U.S. Pat. No. 4,900,735 describes zootechnical compositions of racemic trans Zilpaterol and its derivatives which can be used to increase the rate of weight gain, and improve the feed efficiency and increase carcass leanness in livestock, poultry and fish.

US 2008/0103130 assigned to Pharmacia & Upjohn discloses the preparation of Zilpaterol, and 4-(1,2-dihydro-2-oxobenzo[d]imidazol-3-yl)butanoic acid (compound-iv) also known as buzolic acid (in page 7-8), wherein the said intermediate is prepared by multiple steps: by reacting compound-i (1-(prop-1-en-2-yl)-1H-benzo[d]imidazol-2(3H)-one) with 4-Bromobutyric acid methyl ester in presence base $K_2CO_3$ and acetone to form ester derivative of compound ii; ester derivative converted to acid derivative of compound-iii by hydrolyzing in presence of NaOH in THF. An acid derivative of compound-iii is acidified with hydrochloric acid in presence THF to obtain compound-iv.

The Process is Schematically Represented as Below in Scheme-1:

Scheme-1

[Chem. 3]

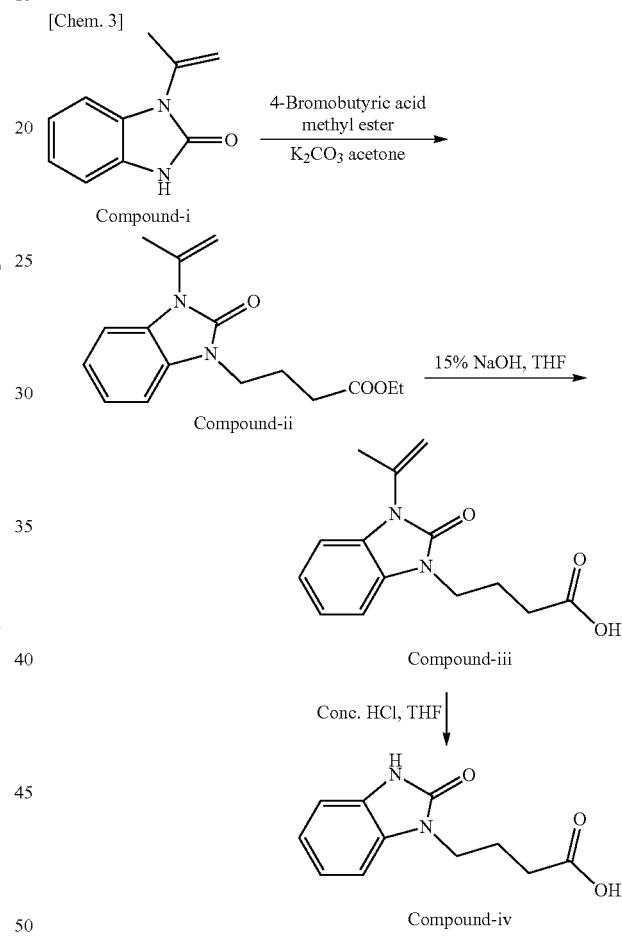

The process for the preparation of Zilpaterol and it's intermediate preparation has been disclosed in Edward J. Salaski, Div. Bio-Org. Chem., Inst. Org. Chem., Syntex Discovery Res., Palo Alto, Calif. 94304, USA; EN)" Synthesis of Imidazobenzazepinethiones: A New Series of HIV-1 Reverse Transcriptase Inhibitors, Tetrahedron Lett. 36 (1995) 9, 1387-1390; wherein the said Compound-6 (4-(1,2-dihydro-2-oxobenzo[d]imidazol-3-yl)butanoic acid) intermediate is prepared by deprotonation of compound-3 (1-(prop-1-en-2-yl)-1H-benzo[d]imidazol-2(3H)-one) with strong base such as sodium hydride in DMF and alkylation of the anion with ethyl 4-bromobutyrate provided the ester compound-4, which was treated with 15% aq NaOH solution in THF to give the acid derivative of compound-5, which is acidified with aq.HCl in presence of DME to produce Compound-6.

The Process is Schematically Represented as Below in Scheme-2:

Scheme-2

[chem. 4]

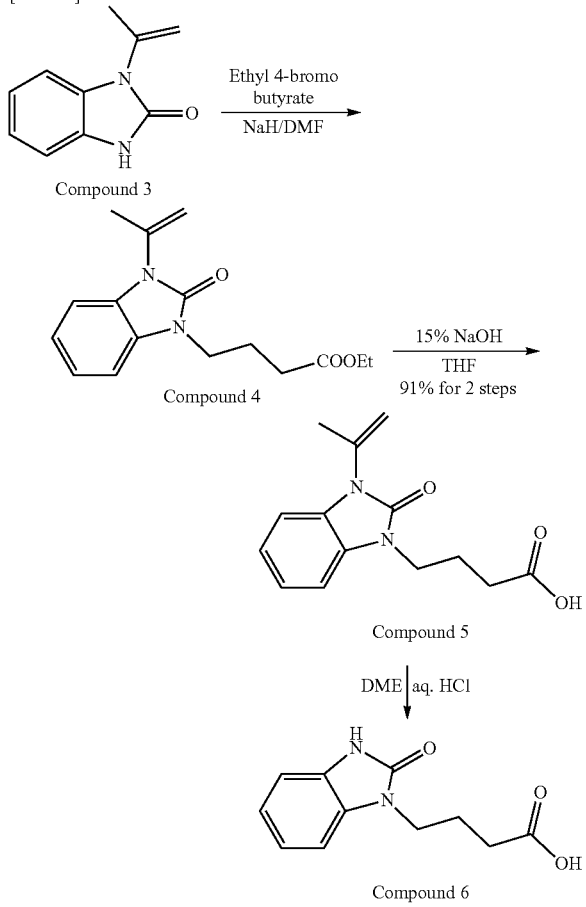

The above mentioned routes for preparation of 4-(1,2-dihydro-2-oxobenzo[d]imidazol-3-yl)butanoic acid have considerable disadvantages, which involve the use of hazardous chemicals which are harmful to the environment and toxic in nature. Further, the isolation of all the intermediates at different stages of preparation makes the process tedious and leads to low yield.

Considering the short comings in the prior art methods, it is imperative to develop an improved method for the preparation of Zilpaterol intermediate of formula (I), which is cost effective, eco-friendly and high yielding with high purity.

Advantageously, the process of the present invention provides a product with significant improvement in the purity i.e. not less than 97% and yield not less than 95%. Further, the one pot process of the present invention uses water as a solvent which effectively contributes to the reduction of overall cost of the process and is also environment friendly.

The present inventors have now found a much simpler, cost effective process with shorter reaction time when compared to the prior art methods.

OBJECT OF THE INVENTION

The main object of the present invention is to provide one pot synthesis for the preparation of 4-(1,2-dihydro-2-oxobenzo[d]imidazol-3-yl)butanoic acid with high purity and yield. Another object of the present invention is to provide industrially viable method for the preparation of formula-I without isolating any intermediates.

SUMMARY OF INVENTION

The main aspect of the present invention is to provide one pot synthesis for the preparation of 4-(1,2-dihydro-2-oxobenzo[d]imidazol-3-yl)butanoic acid of Formula-I.

The present invention involves condensation of methyl-4-chloro butyrate (formula-III) with 1-(prop-1-en-2-yl)-1H-benzo[d]imidazol-2(3H)-one of formula-II in presence of a base and suitable solvent to give corresponding ester derivative, which is hydrolyzed in presence of a base and then acidified with acid to give formula-I with high purity and yield.

DESCRIPTION OF THE EMBODIMENTS

The present invention relates to one pot synthesis of 4-(1,2-dihydro-2-oxobenzo[d]imidazol-3-yl)butanoic acid of Formula-I, which is used as a key intermediate for the preparation of Zilpaterol.

According to the first embodiment the present invention is to provide one pot synthesis of 4-(1,2-dihydro-2-oxobenzo[d]imidazol-3-yl)butanoic acid intermediate of Formula-I.

[Chem. 5]

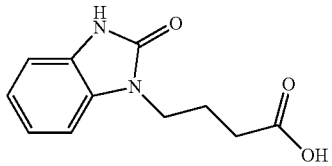

Formula-I which comprises:
(i) condensing methyl-4-halo butyrate of formula-III

[Chem. 6]

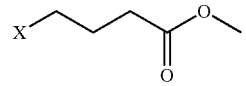

Formula-III

X = halo group (Cl or Br)

with 1-(prop-1-en-2-yl)-1H-benzo[d]imidazol-2(3H)-one of formula II

[Chem. 7]

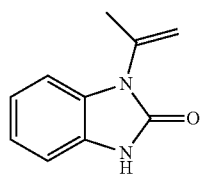

Formula-II in presence of base and suitable solvent to obtain ester derivative.

(ii) hydrolyzing the above ester derivative with base and water to form corresponding salt.

(iii) acidifying the above salt in presence of an acid to form 4-(1,2-dihydro-2-oxobenzo[d]imidazol-3-yl)butanoic acid of Formula-I, wherein the yield not less than 95% and purity is not less than 97%.

The Process is Schematically Represented as Below in Scheme-3:

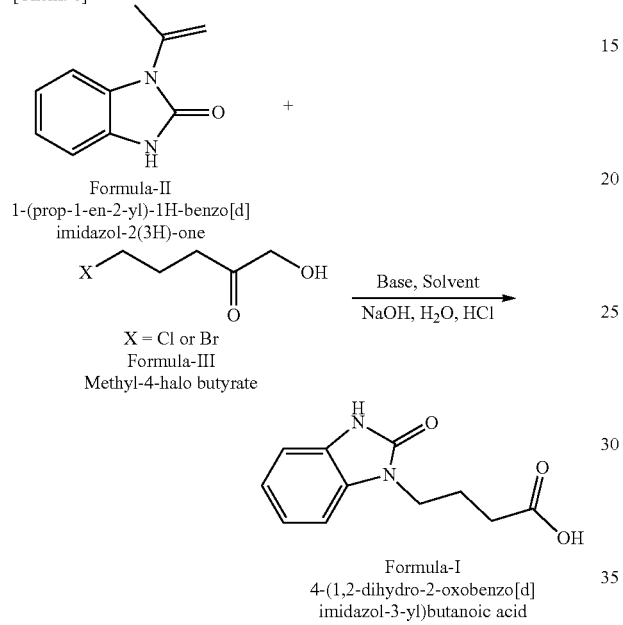

According to one embodiment of the present invention, the base used in condensation step is an inorganic base.

According to another embodiment of the invention, the base used in condensation step is selected from alkali carbonates, alkali bicarbonate, and alkali hydroxides.

According to yet another embodiment of the invention, the base used in condensation step is selected from potassium carbonate, sodium carbonate, potassium bicarbonate, sodium bicarbonate, sodium hydroxide, potassium hydroxide, preferably potassium carbonate.

According to another embodiment of the invention, the suitable solvent used in condensation step is selected from the group comprising DMSO, Acetonitrile, Acetone, Methyl isobutyl ketone preferably DMSO.

According to another embodiment of the invention, hydrolyzation of ester derivative is carried out in presence of base wherein the base is potassium hydroxide, sodium hydroxide, preferably sodium hydroxide.

According to another embodiment of the invention, hydrolyzation is carried out in presence of inorganic solvent wherein the inorganic solvent is preferably Water.

According to yet another embodiment of the present invention, acidification is carried out in presence of acid selected from Hydrochloric acid, Hydrobromic acid, Phosphoric acid, preferably hydrochloric acid.

While the present invention has been described in terms of its specific embodiment, certain modifications and equivalents will be apparent to those skilled in the art and are intended to be included within the scope of the present invention.

Example

Procedure: To a stirred solution of 1-(prop-1-en-2-yl)-1H-benzo[d]imidazole-2(3H)-one (100 gm, 0.57 mole) in DMSO (150 ml) was added potassium iodide (1 gm), TBAB (1 gm), potassium carbonate (104 gm, 0.75 mol), and Methyl-4-chloro butyrate (120 gm, 0.85 mol) was added. After completion of addition, the reaction mixture was stirred for 8-10 hrs at 110-115° C. After completion of reaction, RM was diluted with water and extracted with chloroform and distilled to get crude compound. Water and sodium hydroxide (57 gm, 1.42 mol) was added to the above obtained crude material and stirred for 6 hrs at 95-100° C. and further it was reacted with Conc. HCl (120 ml) and maintained for 5-6 hrs at 80-85° C. Reaction mixture was cooled to room temperature and obtained precipitate was filtered to get 120 gms of 4-(1,2-dihydro-2-oxobenzo[d]imidazole-3-yl)butanoic acid as brown color solid. Yield: 95%, HPLC purity-97%.

The invention claimed is:
1. One pot synthesis for the preparation of 4-(1,2-dihydro-2-oxobenzo[d]imidazol-3-yl)butanoic acid of Formula-I,

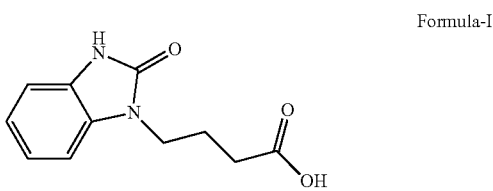 [SMILES: O=C(O)CCCn1c(=O)[nH]c2ccccc21]

which comprises:
(i) condensing methyl-4-chloro butyrate of formula-III with 1-(prop-1-en-2-yl)-1H-benzo[d]imidazol-2(3H)-one of formula II in presence of base and suitable solvent to obtain ester derivative;

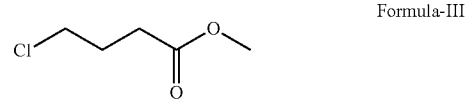

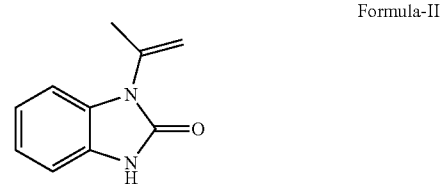

(ii) hydrolyzing the above ester derivative with base and solvent to form corresponding salt; and
(iii) acidifying the above salt in presence of an acid to form 4-(1,2-dihydro-2-oxobenzo[d]imidazol-3-yl)butanoic acid of Formula-I wherein the purity of Formula-I is not less than 97% and yield is not less than 95%.

2. The process as claimed in claim 1, wherein the solvent used in step-ii for hydrolyzing the ester derivative is essentially of water.

3. The process as claimed in claim 1, wherein the base used in step-i is an inorganic base selected from alkali carbonates, alkali bicarbonates and alkali hydroxides.

4. The process as claimed in claim 1, wherein the suitable solvent used in step-i is selected from the group comprising DMSO, acetonitrile, and acetic acid.

5. The process as claimed in claim 1, wherein the base used in step-ii for hydrolyzing the ester derivative is potassium hydroxide, or sodium hydroxide.

6. The process as claimed in claim 1, wherein step-iii acidification is carried out in presence of acid selected from hydrochloric acid, hydrobromic acid, and phosphoric acid.

7. The process as claimed in claim 1, wherein the base used in step-i is an inorganic base selected from potassium carbonate, sodium carbonate, potassium bicarbonate, sodium bicarbonate, potassium hydroxide, and sodium hydroxide.

* * * * *